US009625601B2

(12) United States Patent
Liu et al.

(10) Patent No.: US 9,625,601 B2
(45) Date of Patent: Apr. 18, 2017

(54) NUCLEAR MAGNETIC RESONANCE ROCK SAMPLE ANALYSIS METHOD AND INSTRUMENT WITH CONSTANT GRADIENT FIELD

(75) Inventors: Wei Liu, Beijing (CN); Wei Sun, Beijing (CN); Zhaobin Gu, Beijing (CN); Dianqing Sun, Beijing (CN)

(73) Assignee: PETROCHINA COMPANY LIMITED, Beijing (CN)

( * ) Notice: Subject to any disclaimer, the term of this patent is extended or adjusted under 35 U.S.C. 154(b) by 551 days.

(21) Appl. No.: 14/344,285

(22) PCT Filed: Sep. 28, 2011

(86) PCT No.: PCT/CN2011/001641
§ 371 (c)(1),
(2), (4) Date: Mar. 11, 2014

(87) PCT Pub. No.: WO2013/037093
PCT Pub. Date: Mar. 21, 2013

(65) Prior Publication Data
US 2014/0285196 A1    Sep. 25, 2014

(30) Foreign Application Priority Data
Sep. 14, 2011    (CN) .......................... 2011 1 0272477

(51) Int. Cl.
*G01V 3/14*       (2006.01)
*G01N 24/08*      (2006.01)
(Continued)

(52) U.S. Cl.
CPC ............. *G01V 3/14* (2013.01); *G01N 24/081* (2013.01); *G01R 33/54* (2013.01); *G01R 33/383* (2013.01);
(Continued)

(58) Field of Classification Search
CPC ........ G01V 3/14; G01N 24/081; G01R 33/54; G01R 33/3806; G01R 33/383; G01R 33/445; G01R 33/4835
See application file for complete search history.

(56) References Cited

U.S. PATENT DOCUMENTS 4,710,713 A * 12/1987 Strikman ................. G01V 3/32
                                                                324/303
5,696,448 A    12/1997 Coates et al.
(Continued)

FOREIGN PATENT DOCUMENTS

CN    1193387    9/1998
CN    1707290    12/2005
(Continued)

OTHER PUBLICATIONS

Sun Boqin et al: A global inversin method for multi-dimensional NMR logging:, Journal of Magentic Resonance, vol. 172, No. 1, Jan. 2005, pp. 152-160, XP028548050.
(Continued)

*Primary Examiner* — Rodney Bonnette
(74) *Attorney, Agent, or Firm* — Hahn Loeser & Parks LLP; Bret A. Hrivnak, Esq.

(57) ABSTRACT

The present invention relates to a constant gradient field nuclear magnetic resonance (NMR) rock sample analysis method and instrument. The method includes: in a constant gradient magnetic field, performing NMR measurement to acquire data; converting the measured NMR data into a two-dimensional NMR spectrum $D\text{-}T_2$; performing measurement and inversion on a standard sample of a constant gradient field to obtain a standard sample two-dimensional NMR spectrum $D\text{-}T_2$; measuring the sample to acquire a two-dimensional NMR spectrum $D\text{-}T_2$ of a fluid in the sample; identifying fluid types according to the practically measured two-dimensional NMR spectrum $D\text{-}T_2$; comput-
(Continued)

ing the fluid property and the petrophysical parameters according to the two-dimensional NMR spectrum D-T$_2$ of the fluid in the sample; performing single slice scanning on the sample to acquire partial oil and water saturation; performing continuous slice scanning to obtain axial oil and water saturation distribution and movable fluid saturation distribution of the sample.

6 Claims, 8 Drawing Sheets

(51) Int. Cl.
*G01R 33/54* (2006.01)
*G01R 33/38* (2006.01)
*G01R 33/383* (2006.01)
*G01R 33/44* (2006.01)
*G01R 33/483* (2006.01)

(52) U.S. Cl.
CPC ........ *G01R 33/3806* (2013.01); *G01R 33/445* (2013.01); *G01R 33/4835* (2013.01)

(56) References Cited

U.S. PATENT DOCUMENTS

| 6,111,408 | A | * | 8/2000 | Blades | G01N 24/081 324/303 |
| 7,053,611 | B2 | | 5/2006 | Freedman | |
| 2003/0169040 | A1 | | 9/2003 | Hurlimann et al. | |
| 2003/0214287 | A1 | | 11/2003 | Sun et al. | |
| 2004/0189296 | A1 | * | 9/2004 | Sun | G01V 3/32 324/306 |
| 2011/0234220 | A1 | * | 9/2011 | Mitchell | G01N 24/081 324/303 |

FOREIGN PATENT DOCUMENTS

| CN | 1763563 | 4/2006 |
| CN | 102024546 | 4/2011 |
| CN | 102024546 A | 4/2011 |
| GB | 2402487 A | 12/2004 |
| GB | 2464808 A | 5/2010 |

OTHER PUBLICATIONS

Xie R.-H. et al.: A Method for multiple Echo Trains Jointing Inversion of NMR Relaxation Measurements:, Chinese Journal of Geophysics, vol. 52, No. 6, 2009, pp. 1342-1349, XP002739321.

Database WPI Week 201140 Thomson Scientific, Lond, GB: AN 2011-G17905, XP002739356, Sep. 9, 2009.

* cited by examiner

NUCLEAR MAGNETIC RESONANCE ROCK SAMPLE ANALYSIS METHOD AND INSTRUMENT WITH CONSTANT GRADIENT FIELD

CROSS-REFERENCE TO RELATED APPLICATION

This application is a National Stage entry of International Application No. PCT/CN2011/001641, filed Sep. 28, 2011, which claims priority to Chinese Patent Application No. 201110272477.1 filed Sep. 14, 2011 with the State Intellectual Property Office of the People's Republic of China and each of which are hereby incorporated by reference.

TECHNICAL FIELD

The present invention relates to a constant gradient field nuclear magnetic resonance (NMR) rock sample analysis instrument and a method for identifying fluid types and measuring petrophysical parameters using two-dimensional NMR spectrum.

RELATED ART

In recent years, the NMR technique has been greatly emphasized and developed in the field of petroleum exploration and development and widely applied in all aspects such as NMR cuttings logging, NMR well logging and low permeability reservoir evaluation, thereby promoting the rapid development of NMR instruments and measurement method thereof in petroleum exploration and development.

The equipment and measurement method for measuring petrophysical parameters through NMR relaxation time are described in China Patent 200410083878.2. The equipment includes the parts such as a magnet, a probe, a preamplifier, a power amplifier, an NMR controller, and a control computer. By obtaining one-dimensional relaxation time $T_2$ spectrum through measurement, the equipment may rapidly gives petrophysical parameters, such as porosity, permeability, movable fluid saturation and oil saturation.

In addition to the relaxation time $T_2$, the NMR instrument may further provide a fluid diffusion coefficient D. Currently, all laboratory NMR instruments capable of measuring a fluid diffusion coefficient utilize an electrical gradient, acquire a gradient magnetic field by adopting an electrical current manner, and control the magnitude and direction of a gradient field by adopting an electrical current, and such a manner is also widely applied in medical NMR instruments. However, as the diffusion coefficient of crude oil is small in petroleum exploration and development, a large gradient field is required to measure the diffusion coefficient of crude oil to identify oil and water. The magnitude of the gradient field depends on the magnitude of a transient electrical current; however, the transient electrical current cannot be amplified infinitely and the magnitude thereof is limited by instruments. Especially, when the generated transient electrical current is larger, the system becomes more complicated.

Currently, in a dynamic displacement test of an NMR instrument, after the displacement, a rock core is removed to perform NMR measurement. The NMR high-temperature and high-pressure NMR test cannot be performed. It is mainly because that the electrical magnetic field of the NMR instrument is unable to pass through the metal shell and a gradient magnetic field cannot be formed inside the probe, resulting in that diffusion encoding cannot be performed and the diffusion coefficient of a fluid cannot be measured. All these constrain the development of the NMR laboratory technique.

Therefore, a constant gradient field NMR rock sample analyzer capable of measuring a diffusion coefficient and performing a high-temperature and high-pressure test and a method for identifying fluid types and evaluating petrophysical parameters by obtaining a two-dimensional NMR spectrum are urgently needed.

SUMMARY

An object of the present invention is to provide a constant gradient field NMR rock sample analyzer and a measurement method, so as to measure petrophysical parameters and fluid property parameters such as diffusion coefficient, relaxation time, oil viscosity, porosity, permeability, oil and water saturation and distribution, movable fluid saturation, thereby solving the difficult problems in fluid identification and reservoir evaluation in petroleum exploration and development, enhancing the levels of indoor NMR equipment and techniques, satisfying the exploration and development demands of oil and gas field, and promoting rapid development of the NMR rock sample technique in the fields of petroleum exploration and development.

The technical solution adopted in the present invention includes: a constant gradient field NMR rock sample analyzer formed of a measuring device 1 and a control system 4; where the measuring device 1 is formed of a gradient magnet 2, a probe 3 and a temperature control system; the gradient magnet 2 is an enclosed cavity, the probe 2 is located at the central position of the gradient magnet cavity, the probe 2 and the control system 4 are connected to a T/R matching circuit 10 of the control system 4 through an electrical cable; and the control system 4 is connected to a computer through a USB port.

The gradient magnet 2 of the constant gradient field NMR rock sample analyzer is formed of a yoke plate 14, a magnetic steel 15, a polar plate 16, and a side yoke plate. The yoke plate 14 and the side yoke plate form a gradient magnet cavity. The magnetic steel 15 and the yoke plate 14 are connected. The cross section of the polar plate 16 has a trapezoidal structure and is connected to the magnetic steel 15. The yoke plate, the polar plate, and the side yoke plate are machined from an electrical pure iron DT4 C material, and the magnetic steel is made of 2:17 SmCo magnetic material. The magnetic steel 15 and the yoke plate 14, and the polar plate 16 and the magnetic steel are adhered by using the glue BJ-39. The gradient magnet 2 generates a magnetic field $B_0$ which is longitudinally uniform and has horizontal gradients to form a sample detection area. The magnetic field direction is along the z-axis, whereas the gradient direction is along the x-axis. The angle between the two polar plates is between 10° and 30°. An air gap formed between the two polar plates is between 150 mm and 364 mm. (See a gradient permanent magnet for a constant gradient field rock sample analyzer disclosed in Patent 200910092839.1). The outer surface of the gradient magnet 2 is a group of temperature control systems 6, which performs constant temperature control on the gradient magnet between 10° and 60°, so as to reduce the influences of temperature on the measurement result of the instrument.

The probe 3 of the constant gradient field NMR rock sample analyzer is formed of a nonconductive circular sample tube 18 and a loop circuitry 19. The loop circuitry 19 is wound on the sample tube 18. The loop circuitry 19 is a solenoid coil, a saddle coil or other applicable coils. The probe may transmit an excitation signal into a sample to be tested in a radio frequency manner as a transmitter and may receive NMR information as a receiver. A sample detection area 20 is provided inside the probe 3. Particularly, an NMR high-temperature high-pressure probe may be placed in the constant gradient field NMR rock sample analyzer.

The control system 4 of the constant gradient field NMR rock sample analyzer is formed of a main controller 7, a frequency generator 8, a power amplifier 9, a T/R matching circuit 10, a preamplifier 11, a receiver 12 and an A/D converter with a buffer 13. The main controller 7 mainly has three functions: generating and transmitting a pulse sequence for exciting NMR signals, receiving NMR echo signals and performing computation processing on the signal and an upload to a computer. The main controller 7 and the computer 5 are interconnected through a USB interface and perform data transmission. The frequency generator 8 and the main controller 7 are interconnected through an electrical cable. The frequency generator performs electrical current driving on the NMR excitation signal generated by the main controller. The generated signal is sent to the power amplifier 9 for power amplification. The power amplifier 9 and the frequency generator 8 are interconnected through an electrical cable. The power amplifier may amplify a signal to hundreds of Watts, and is used for exciting the NMR information of a sample to be tested. The probe 3 and the transmitter/receiver (T/R) matching circuit 10 usually include a resonant capacitor, a T/R switch and an impedance matching circuit, and are connected to the power amplifier 9 and the preamplifier 11 by an electrical cable. To acquire more accurate echo signal data, it is required to receive an echo signal within a time as short as possible after a radio frequency excitation signal is transmitted. The T/R transmission/reception switch may accomplish such a conversion process rapidly and effectively. The impedance matching circuit is used for perform impedance matching on the radio frequency circuit. The preamplifier amplifies the NMR echo signal by about 70 DB. After the amplification of the magnitude, the NMR echo signal may be collected and received by the receiver 12, and then be output to the main controller 7 with an A/D converter with a buffer 13, so as to provide the required output data for subsequent use and analysis. The preamplifier 11 and the receiver 12, and the receiver 12 and the A/D converter 13 are connected through electrical cables.

Meanwhile, the system further includes an auxiliary equipment computer 5 for controlling the control system, thereby controlling the whole instrument. The computer 5 is connected to the main controller 7 in the control system 4 through a USB port.

The measurement method of the constant gradient field NMR rock sample analyzer may include: Step A: design of the constant gradient field pulse sequences and parameters; Step B: acquisition of two-dimensional NMR spectrums; Step C: calibration of the constant gradient field NMR; Step D: identification of fluid types; Step E: computation of petrophysical parameters; and Step F: acquisition of axial saturation distribution of a rock sample.

Step A: Design of the Constant Gradient Field Pulse Sequences and Parameters

Pulse sequences are the soul of the NMR technique, which decide the application fields of the NMR. The present invention relates to a CGMF-CPMG pulse sequence. A time interval between a 90° pulse and a 180° pulse is a pulse interval tau the unit: us, and $N_k$ is the number of pulse intervals tau. When k=1, the value of the pulse interval tau is $tau_{N_1}$, one 90° pulse is followed by $P_1$ 180° pulses, and at this time the CGMF-CPMG pulse sequence is simplified into a CPMG pulse sequence; when k=2, one 90° pulse is followed by $P_2$ 180° pulses; . . . ; and when it is k, one 90° pulse is followed by $P_k$ 180° pulses. The principle of the technique is that the intensity of an NMR signal is attenuated due to the Brownian motion of molecules, and such attenuation is related to the diffusion coefficient of fluid molecules. The effect of the 90° pulse is to rotate the macro magnetization vector onto the horizontal plane; the effect of continuous 180° pulses is to focus again the signals that are not subject to the phase defocusing caused by diffusion attenuation, and acquire information of other mechanisms of spin echo attenuation $T_2$. A diffusion effect is generated through changing the value of tau in the CGMF-CPMG pulse sequence in the constant gradient field. The constant gradient field is generated by the magnet and keeps acting on the sample detection area.

According to the saturated fluid in the sample under test, the parameters including the echo train k, pulse interval tau, the number of 180° pulses Ne, and the waiting time RD in the CGMF-CPMG pulse sequence are designed to perform NMR measurement to acquire measurement data; the value of k is between 2 and 8, the value of tau is distributed between 150 us and 20000 us, the value of Ne is distributed between 128 and 30720, and the waiting time is distributed between 2000 ms and 12000 ms.

Step B: Acquisition of Two-Dimensional NMR Spectrums

The applications of the NMR technique in the petroleum industry are mainly to measure the signal of saturated fluid hydrogen nucleuses in the rock pore by adopting an NMR instrument. These applications are not only related to the fluid itself, but also further influenced by the pore structure of rock. The influence factors of relaxation time of hydrogen nucleuses in the fluid include body relaxation, surface relaxation and diffusion relaxation. The body relaxation $T_{2B}$ is the process of energy transfer between the spin nucleuses and lattice. The relaxation time is influenced by the spin-spin coupling effect and resonance frequency. The surface relaxation $T_{2S}$ is the mutual effect between pore fluid molecules in a porous medium, and the relaxation time and the surface relaxation rate is related to the specific surface of pore. The diffusion relaxation is related to the diffusion coefficient D, magnetic field gradient G, and pulse interval tau. Therefore, the expression of the $T_2$ relaxation time in the rock pore is:

$$\frac{1}{T_{2App}} = \frac{1}{T_{2B}} + \frac{1}{T_{2S}} + \frac{1}{T_{2D}} \tag{1}$$

In the equation: $T_{2app}$ is the apparent relaxation time, $T_{2B}$ is the body relaxation time, $T_{2S}$ is the surface relaxation time, and $T_{2D}$ is the diffusion relaxation time.

For $T_{2S}$:

$$\frac{1}{T_{2S}} = \rho \frac{S}{V} \text{ where: } \frac{S}{V} \tag{2}$$

is the specific surface of a pore, and $\rho$ is the surface relaxation rate.

For $T_{2D}$:

$$\frac{1}{T_{2D}} = \frac{1}{3} D(\gamma G tau)^2 \tag{3}$$

where: D is the diffusion coefficient of the fluid, γ is the gyromagnetic ratio constant, G is the magnetic field gradient, and tau is the pulse time interval.

The signal b(t,tau) measured according to the pulse sequence of the constant gradient field in Step A is generally expressed as:

$$b(t,tau)=\iiint f(D,T_2)k_2(t,T_E,D,T_2)dDdT_2\epsilon \quad (4)$$

The discrete form is:

$$b_{ik} = \sum_{j=1}^{m}\sum_{l=1}^{p} f_{lj}\exp\left(-\frac{1}{12}\gamma^2 G^2 tau_k^2 D_l t_i\right)\exp(t_i/T_{2j}) + \varepsilon_{ik} \quad (5)$$

The relaxation time and the diffusion coefficient are uniformly distributed on the axes of a logarithmic coordinate system, and Equation (5) is simplified into:

$$b_{ik}=f_{lj}E_{ik,lj}+\epsilon_{ik} \quad (6)$$

where: i=1, . . . , $n_k$, k=1, . . . , q, l=1, p, and j=1, . . . , m;
 i denotes the ith echo of the kth echo train, dimensionless;
 k denotes the kth echo train, dimensionless;
 l denotes the lth diffusion coefficient selected in advance, dimensionless;
 j denotes the jth relaxation time selected in advance, dimensionless;
 $n_k$ is the number of echoes of the kth echo train, dimensionless;
 q is the number of echo trains of different $tau_k$, dimensionless;
 p denotes the number of diffusion coefficients selected in advance;
 m denotes the number of relaxation times selected in advance;
 $b_{ik}$ denotes the amplitude of the ith echo of the kth echo train with the pulse interval being $tau_k$ dimensionless;
 $f_{lj}$ denotes the amplitude when the diffusion coefficient is $D_l$ and the relaxation time is $T_{2j}$, dimensionless;

$$E_{ik,lj} = \exp\left(-\frac{1}{12}\gamma^2 g^2 T_{E_k}^2 D_l t_i\right)\exp(-t_i/T_{2j});$$

γ is the gyromagnetic ratio, unit: MHz/T;
 G is the magnetic field gradient, unit: Gauss/cm;
 $tau_k$ is the pulse interval of the kth echo train, unit: us.

The matrix form of Equation (6) is:

$$\begin{bmatrix} b_{11} \\ \vdots \\ b_{n_11} \\ b_{12} \\ \vdots \\ b_{n_22} \\ \vdots \\ \vdots \\ \vdots \end{bmatrix} = \quad (7)$$

$$\begin{bmatrix} E_{11,11} & \cdots & E_{11,1m} & E_{11,2m} & \cdots & E_{11,pl} & \cdots & E_{11,pm} \\ \vdots & & & & & & & \\ E_{n_11,11} & \cdots & & & & & & \\ E_{12,11} & \cdots & & & & & & \\ \vdots & & & & & & & \\ E_{n_2,11} & \cdots & & & & & & \\ \vdots & & & & & & & \\ \vdots & & & & & & & \\ \vdots & & & & & & & \end{bmatrix} \begin{bmatrix} f_{11} \\ \vdots \\ f_{1m} \\ f_{21} \\ \vdots \\ f_{2m} \\ \vdots \\ f_{pl} \\ \vdots \\ f_{pm} \end{bmatrix}$$

Components that are smaller than zero probably exist in the calculated magnitude of the two-dimensional NMR spectrum, which is physically illogical. When Equation 7 is being solved, non-negative constraint further needs to be added, that is, $f_{ij}\geq 0$. The matrix E in Equation 7 is highly singular, the condition number is large, and the practically measured signal cause significant challenges to inversion with noise interferences.

In the present invention, an improved singular value decomposition method is adopted for inversion to acquire a two-dimensional NMR spectrum. The singular value decomposition method gives one optimal solution in the sense that $\|Ef-b\|_2$ is minimal, which does not necessarily meet a non-negative constraint condition. In a conventional SVD algorithm, through E reduction iterative solution, the number of dimensions of the solutions is reduced, and the coordinate component that has the largest oscillation is missing. Due to the absence of this part of coordinate component, the spectrum is discontinuous. To acquire a continuous spectrum, the improved singular value decomposition method solves the least squares solutions of Δf. Assuming that one initial solution is known, make $b_0=Ef_0$, so the original equation may become: $E(f-f_0)=b-b_0$, that is, $E\Delta f=\Delta b$. If the optimal solution Δf in the sense of minimal $\|E\Delta f-\Delta b\|_2$ is obtained, $f_0+\Delta f$ is the optimal solution f in the sense of minimal $\|Ef-b\|_2$. As Δf is to be solved, during the implementation of non-negative constraints, the matrix E is no longer reduced, and only the components of f that are smaller than zero are changed to zero, and then iterative computation is performed for Δf again, until all coordinate components of f meet the non-negative constraints. As E does not change during the iterative solution, singular value decomposition is no longer required for solving the optimal solution in the sense of minimal $\|E\Delta f-\Delta b\|_2$. Compared with the original algorithm, the new algorithm replaces the singular value decomposition process of matrix E with the computation of Δf and Δb, and does not need to perform singular value decomposition on the matrix E for cycling each time, which greatly reduces the computation amount and computation time.

Step C: Calibration of Constant Gradient Field NMR

Calibration is an essential step to measure the sample porosity of a rock in the NMR technique. The calibration of a constant gradient field NMR rock sample analyzer performs measurement and inversion on standard samples of the constant gradient field by adopting a constant gradient field NMR rock sample analyzer according to Step A and Step B to obtain two-dimensional NMR spectrums $D-T_2$ of the standard sample and acquire a relationship line between signal and porosity for a unit volume. The constant gradient field NMR standard sample includes 12 in total, and the porosities are 0.5%, 1%, 2%, 3%, 6%, 9%, 12%, 15%, 18%, 21%, 24%, and 27%, respectively. At least 5 of them are selected for measurement in calibration each time, and the main steps are as follows:

(1) placing a standard sample in the probe of the constant gradient field NMR rock sample analyzer to perform measurement by adopting a pulse sequence parameter designed in advance to obtain a set of multi-exponential attenuation data;

(2) inputting the volume and porosity of a standard sample, and performing normalization processing on a sample NMR signal to obtain the signal quantity of a unit volume of the sample; (3) repeating Step (1) and Step (2) to measure standard samples of different porosities;

(4) performing linear fitting automatically to obtain a calibration curve of the two-dimensional NMR spectrum by software system. The relationship between the NMR signal and porosity for a unit volume is:

$$y = ax + b \qquad (8)$$

where, y represents the NMR signal quantity of a unit volume, x represents an NMR porosity (%), a represents a slope, and b represents a Y-intercept.

Step D: Identification of Fluid Types

According to Step A and Step B, a two-dimensional NMR spectrum $D$-$T_2$ of a practical rock sample is acquired to identify fluid types. One dimension of the two-dimensional NMR spectrum is a diffusion coefficient D, and the other dimension is relaxation time $T_2$, so that the diffusion coefficient and relaxation time of a sample under test can be acquired at the same time through a two-dimensional NMR spectrum. As bulk phase fluids, for example, crude oil, natural gas and water, not only have different relaxation time $T_2$, but also have different diffusion coefficients D, so that a two-dimensional NMR spectrum may be adopted to identify fluid types rapidly. The diffusion coefficient of bulk phase fluid water is a constant, and is related to temperature. The diffusion coefficient of a gas is related to temperature and pressure. A linear relationship exists between the diffusion coefficients and the relaxation times of crude oil:

$$D_w(T_2) = D_w(T) \qquad (9)$$

$$D_g(T_2) = D_g(T,P) \qquad (10)$$

$$D_o = \alpha T_2 \qquad (11)$$

The constant gradient field NMR rock sample analyzer establishes a two-dimensional NMR spectrum explanation template according to such attributes of diffusion coefficient and relaxation time of oil, gas and water, so as to identify fluid types rapidly.

The fluid in the pore is influenced by the pore surface, and the relaxation time and diffusion coefficient are influenced differently, resulting in that on a one-dimensional relaxation time $T_2$ spectrum or a one-dimensional diffusion coefficient D spectrum, a part of signals of oil and water overlap each other, making direct distinguishing impossible. The two-dimensional NMR spectrum $D$-$T_2$ adds a one-dimensional diffusion coefficient on the basis of the one-dimensional relaxation time $T_2$ spectrum, so that the fluid types in the pore can be better identified from the 3D space.

Step E: Computation of Petrophysical Parameters

The constant gradient field NMR rock sample analyzer is applicable to the measurement of relaxation and diffusion properties of a fluid, and particularly fluid properties in a rock pore. As these properties are different for oil, gas and water, the constant gradient field NMR rock sample analyzer can provide the proportion of oil, gas and water, and parameters such as rock porosity, permeability, oil saturation, movable fluid saturation, crude oil coefficient, and especially may acquire axial oil saturation distribution and water saturation distribution of a rock sample.

(1) Porosity

The NMR technique directly detects the hydrogen nucleus ($^1$H) in a sample and may accurately measure the amount of fluid in the pores of a rock sample. When the pores of the rock sample are filled with a fluid, the fluid amount is equal to the pore volume. Therefore, the porosity of the rock sample may be accurately measured by using the NMR technique.

It can be obtained through Equation (8):

$$x = \frac{1}{a}(y - b) \qquad (12)$$

When the two-dimensional NMR spectroscopy is adopted to measure the porosity of a rock sample, first, it has to be guaranteed that the rock sample is fully saturated; next, calibrating is performed by adopting a constant gradient field NMR standard sample to acquire a calibration line of the two-dimensional NMR spectrum, that is, the relationship between the NMR signal and the porosity for a unit volume; finally, the measured NMR signal of the fluid in the saturated rock sample is introduced in Equation (12) to acquire the NMR porosity of the rock sample.

(2) Oil Saturation

Oil saturation is one of the key parameters for evaluating the quality of an oil field reservoir. The key for the measurement of oil saturation is to distinguish oil and water. The two-dimensional NMR spectrum may measure the relaxation time and diffusion coefficient of oil and water, and fluid types can be rapidly identified according to a two-dimensional NMR spectrum explanation template to distinguish oil and water. The constant gradient field NMR rock sample analyzer software may adopt a click and selection manner to compute oil saturation. The area of oil in the two-dimensional NMR spectrum is selected with a mouse, and the computer automatically computes a ratio between the volume integral of the selected area and the total volume integral to acquire oil saturation. Similarly, the saturation of oil, gas and water may be obtained respectively.

(3) Movable Fluid Saturation

The relaxation time spectrum $T_2$ reflects the distribution of pore diameters of a rock. When the pore diameter is small to a certain degree, the fluid in the pore is constrained by the capillary force and fails to flow. Therefore, a limit exists on the $T_2$ relaxation time spectrum. When the relaxation time of pore fluid is greater than a certain relaxation time, the fluid is movable fluid, and otherwise it is irreducible fluid. Such a relaxation time limit is referred to as the cutoff value of the movable fluid. The cutoff value of the movable fluid $T_2$ usually needs to be determined by combining the NMR and centrifugation. The cutoff value on the one-dimensional relaxation time $T_2$ spectrum is a cutoff line on the two-dimensional NMR spectrum. The two-dimensional NMR spectrum may be judged comprehensively according to the cutoff line, the diffusion coefficient line, oil phase relationship line and the like to select a movable fluid area, the system automatically computes a ratio between the volume integral of the selected area and the total volume integral to acquire the movable fluid saturation. Similarly, the movable water saturation and irreducible water saturation may be acquired. The movable fluid saturation has become one important index for reservoir evaluation, and the research on movable fluid saturation is very important for exploration and exploitation of low permeability oil fields.

(4) Permeability

The two-dimensional NMR spectrum reflects the formation pore diameter distribution, whereas a certain relationship exists between the formation rock permeability and the pore diameter (pore throat). Therefore, the permeability of the rock sample may be computed according to the two-dimensional NMR spectrum. The test shows that the empirical Equation 11 may be adopted to compute the permeability of a rock sample.

$$K_{nmr} = \left(\frac{\phi_{nmr}}{C}\right)^4 \left(\frac{100\% - S_{wi}}{S_{wi}}\right)^2 \quad (13)$$

where, $K_{nmr}$ is the NMR permeability, $\phi_{nmr}$ is the NMR porosity, $S_{wi}$ is the irreducible water saturation, C is a coefficient to be determined, which has regional empiricism and needs to be precisely determined through indoor NMR rock core analysis. The NMR permeability computed according to the empirical Equation (13) desirably solves the problem of small NMR permeability of rock sample having high oil saturation and high oil density during the computation according to Coates model.

(5) Crude Oil Coefficient

Crude oil with different properties has a different NMR signal quantity in unit volume. This is because crude oil has complicated components and the contents of all components are different. As high-density crude oil has a large quantity of heavy components, especially thick oil has high colloidal asphaltene, the ratio of carbon and hydrogen is large, and the unit volume has a small NMR signal quantity. Therefore, when a rock sample contains crude oil with a high viscosity, the NMR signal for a unit volume of measured rock sample is small, causing offsets of different degrees to the parameters of a rock sample, such as permeability, movable fluid saturation and oil saturation, which have to be calibrated. Therefore, a crude oil coefficient η is introduced, that is, a ratio between the signal quantity of a unit volume of constant gradient field NMR standard sample and the NMR signal quantity of a unit volume of crude oil:

$$\eta = \frac{A_{Standard\ Sample} / \phi_{Standard\ Sample}}{A_{Crude\ Oil}} \quad (14)$$

where: η is the crude oil coefficient, $A_{Standard\ Sample}$ is the NMR signal quantity of a unit volume of the standard sample, $\phi_{Standard\ Sample}$ is the porosity of a standard sample, and $A_{Crude\ oil}$ is the NMR signal quantity of a unit volume of the measured crude oil.

After the crude oil coefficient is introduced, as both the signal and total signal of the crude oil have changed, the parameters such as movable fluid saturation, irreducible water saturation, movable water saturation need to be computed by selecting an area again according to the explanation template. The equations need to be modified for parameters such as porosity, permeability, and oil saturation.

The modified equation of oil saturation by the crude oil coefficient:

$$S_{Oil,Modified} = \frac{A_{Oil} \times \eta}{A_{Water} + A_{Oil} \times \eta} \times 100\% \quad (15)$$

The modified equation of porosity by the crude oil coefficient:

$$\phi_{Modified} = 1/a(A_{Oil} \times \eta + A_{water} - b)/100\% \quad (16)$$

The modified equation of permeability by the crude oil coefficient:

$$K_{Modified} = \left(\frac{\phi_{Modified}}{C}\right)^4 \left(\frac{1 - S_{wi,Modified}}{S_{wi,Modified}}\right)^2 \quad (17)$$

where, $\phi_{Modified}$ is the modified NMR porosity, $K_{Modified}$ is the modified NMR permeability, η is the crude oil coefficient, $S_{Oil,Modified}$ is the modified oil saturation, $A_{Oil}$ is the oil signal quantity, $A_{Water}$ is the water signal quantity, $S_{wi,Modified}$ and the modified irreducible water saturation.

Step F: Acquisition of Axial Saturation Distribution of a Rock Sample

The slicing thickness of the constant gradient field NMR rock sample analyzer is 0.3 cm, and according to Step A to Step F, slice scanning may be performed on a rock sample to acquire partial oil and water saturation of a rock sample; at the same time, Step A to Step F are repeated to perform continuous slice scanning on the rock sample to acquire axial oil and water saturation distribution and movable fluid saturation distribution of the rock sample, so as to perform better real-time reservoir evaluation and fluid identification, especially the evaluation of oil and gas reservoirs of low porosity, low permeability and complicated reservoir.

BRIEF DESCRIPTION OF THE DRAWINGS

The present disclosure will become more fully understood from the detailed description given herein below for illustration only, and thus are not limitative of the present disclosure, and wherein:

FIG. 3 is a flow chart of a method that a constant gradient field NMR rock sample analyzer measures petrophysical parameters of a rock sample, identifies fluid types and acquires oil and water saturation distribution, and the like;

DETAILED DESCRIPTION

Figure 1:
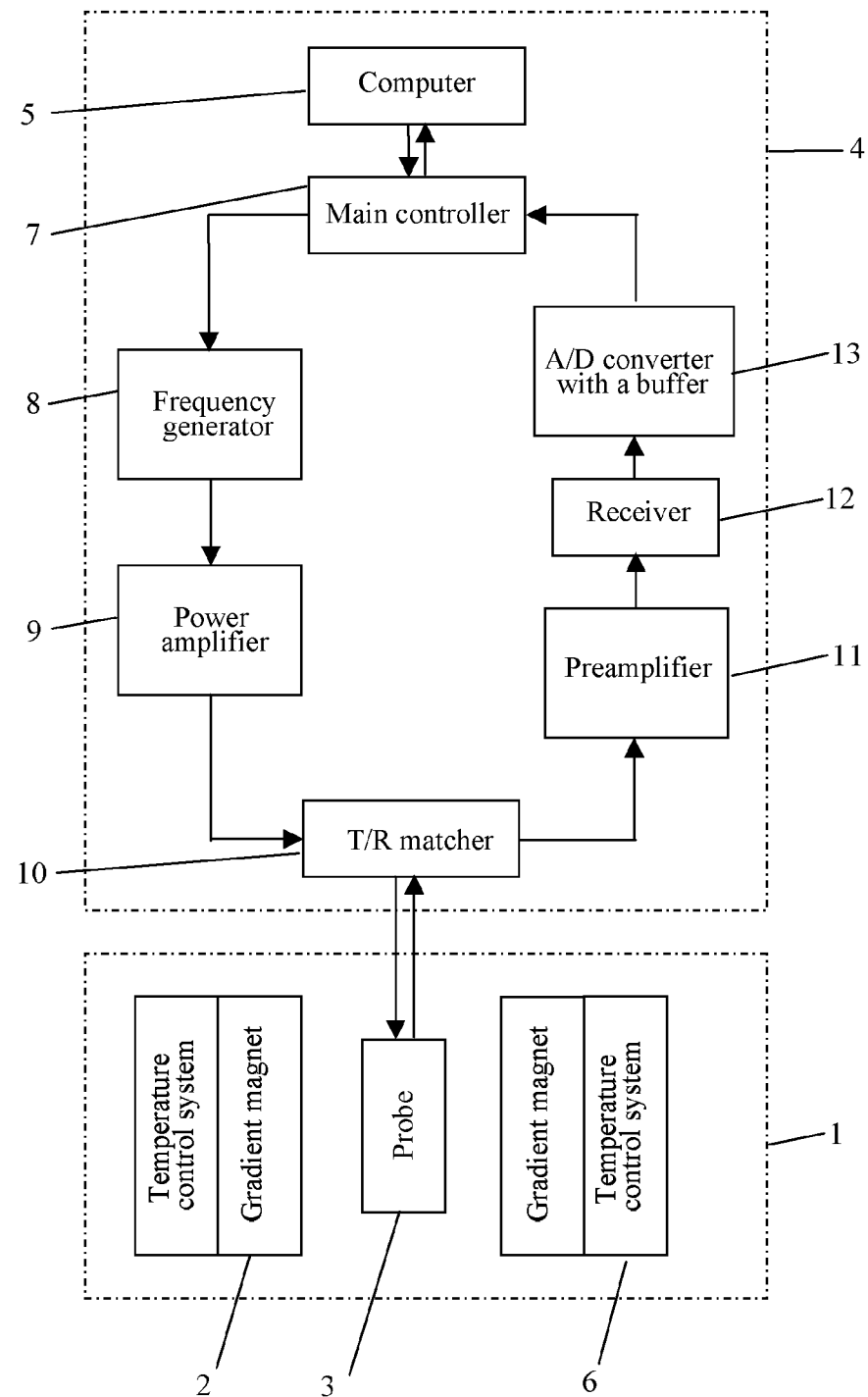
FIG. 1 is a block diagram, which shows a constant gradient field NMR rock sample analyzer.
Figure 2:
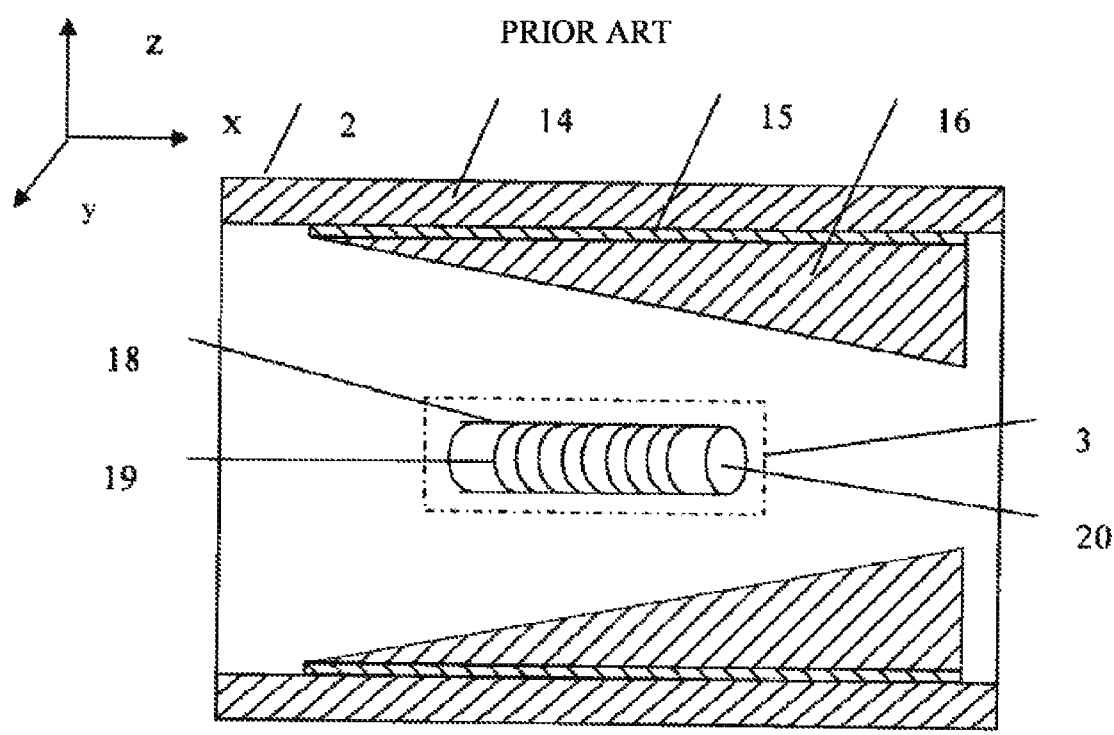
FIG. 2 is a schematic structural diagram of a measuring device of a constant gradient field NMR rock sample analyzer, which mainly includes a gradient magnet and probe.

A constant gradient field NMR rock sample analyzer is formed of a gradient magnet 2, a probe 3, a control system 4 and an auxiliary equipment computer 5. The gradient magnet 2 is one separately enclosed cavity. The probe 2 is located at the central position of the gradient magnet cavity, and forms a measuring device 1 together with the gradient magnet. The probe 2 and the control system 3 are connected through an electrical cable. The control system 3 and the computer are connected through a USB port.

The gradient magnet 2 of the constant gradient field NMR rock sample analyzer is formed of a yoke plate 14, a magnetic steel 15, a polar plate 16, and a side yoke plate. The magnetic steel 15 and the yoke plate 14 are connected, the polar plate 16 and the magnetic steel 15 are connected, and the magnet polar plate 16 adopts soft iron with a trapezoidal cross section. The yoke plate, the polar plate, and the side yoke plate are processed from an electrical pure iron DT4C material. The magnetic steel is made of a 2:17 SmCo magnetic material. The magnetic steel 15 and the yoke plate 14, and the polar plate 16 and the magnetic steel are adhered by using the glue BJ-39. The gradient magnet 2 generates a magnetic field $B_0$ which is longitudinally uniform and has horizontal gradients to form a sample detection area. The magnetic field direction is along the z-axis, whereas the gradient direction is along the x-axis. The angle between the two polar plates is between 10° and 30°. An air gap formed between the two polar plates is between 150 mm and 364 mm. (See a gradient permanent magnet for a constant gradient field rock sample analyzer disclosed in Patent 200910092839.1). The outer surface of the gradient magnet 2 is a group of temperature control systems 6, which performs constant temperature control on the gradient magnet between 10° and 60°, so as to reduce the influences of temperature on the measurement result of the instrument.

The probe 3 of the constant gradient field NMR rock sample analyzer is formed of a nonconductive circular sample tube 18 and a loop circuitry 19. The loop circuitry 19 is wound on the sample tube 18. The loop circuitry 19 is a solenoid coil, a saddle coil or other applicable coils. The probe may transmit an excitation signal into a sample to be tested in a radio frequency manner as a transmitter and may receive NMR information as a receiver. A sample detection area 20 is provided inside the probe 3. Particularly, an NMR high-temperature high-pressure probe may be placed in the constant gradient field NMR rock sample analyzer.

The control system 4 of the constant gradient field NMR rock sample analyzer is formed of a main controller 7, a frequency generator 8, a power amplifier 9, a T/R matching circuit 10, a preamplifier 11, and a receiver 12. The main controller 7 mainly has three functions: generating and transmitting a pulse sequence for exciting an NMR signal, receiving an NMR echo signal and performing computation processing on the signal and an upload to a computer. The main controller 7 and the computer 5 are interconnected through a USB interface and perform data transmission. The frequency generator 8 and the main controller 7 are interconnected through an electrical cable. The frequency generator performs electrical current driving on the NMR excitation signal generated by the main controller. The generated signal is sent to the power amplifier 9 for power amplification. The power amplifier 9 and the frequency generator 8 are interconnected through an electrical cable. The power amplifier may amplify a signal to hundreds of Watts, and is used for exciting the NMR information of a sample to be tested. The probe 3 and the transmitter/receiver (T/R) matching circuit 10 usually include a resonant capacitor, a T/R switch and an impedance matching circuit, and are connected to the power amplifier 9 and the preamplifier 11 by an electrical cable. To acquire more accurate echo signal data, it is required to receive an echo signal within a time as short as possible after a radio frequency excitation signal is transmitted. The T/R transmission/reception switch may accomplish such a conversion process rapidly and effectively. The impedance matching circuit is used for perform impedance matching on the radio frequency circuit. The preamplifier amplifies the NMR echo signal by about 70 DB. After the amplification of the magnitude, the NMR echo signal may be collected and received by the receiver 12, and then be output to the main controller 7 with an A/D converter with a buffer 13, so as to provide the required output data for subsequent use and analysis. The preamplifier 11 and the receiver 12, and the receiver 12 and the A/D converter 13 are connected through electrical cables.

Meanwhile, the system further includes an auxiliary equipment computer 5 for controlling the control system, thereby controlling the whole instrument. The computer 5 is connected to the main controller 7 in the control system 4 through a USB port.

Figure 3:
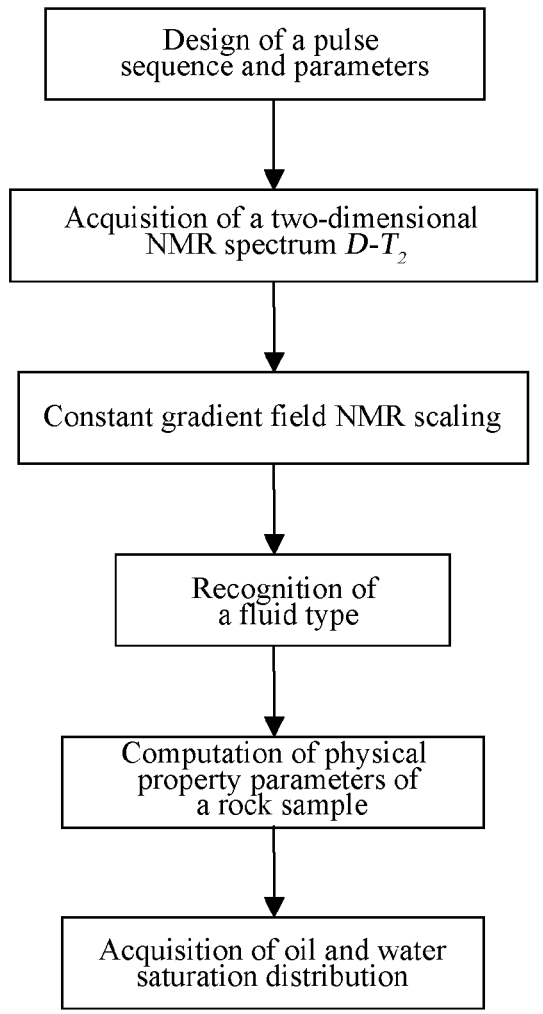
Figure 4:
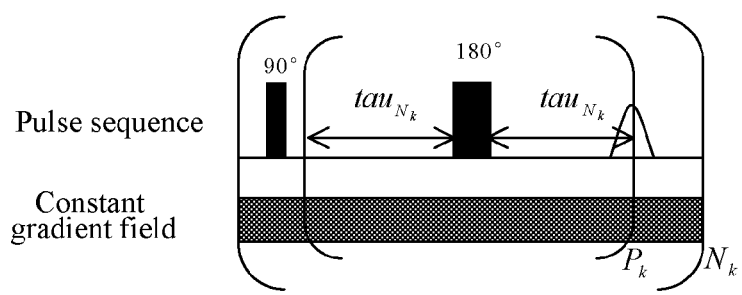
FIG. 4 shows a CGMF-CPMG pulse sequence for NMR measurement in a constant gradient field.

The measurement method of the constant gradient field NMR rock sample analyzer may include: Step A: design of the constant gradient field pulse sequences and parameters; Step B: acquisition of two-dimensional NMR spectrums; Step C: calibration of constant gradient field NMR; Step D: identification of fluid types; Step E: computation of petrophysical parameters of a rock; and Step F: acquisition of axial saturation distribution of a rock sample. FIG. 3 is a flow chart of a method that a constant gradient field NMR rock sample analyzer measures petrophysical parameters of a rock sample, identifies fluid types and acquires oil and water saturation distribution, and the like.

Step A: Design of the Constant Gradient Field Pulse Sequences and Parameters

Pulse sequences are the soul of the NMR technique, which decide the application fields of the NMR. The present invention relates to a CGMF-CPMG pulse sequence. A time interval between a 90° pulse and a 180° pulse is a pulse interval tau the unit: us, and $N_k$ is the number of pulse intervals tau. When k=1, the value of the pulse interval tau is $tau_{N1}$, one 90° pulse is followed by $P_1$ 180° pulses, and at this time the CGMF-CPMG pulse sequence is simplified into a CPMG pulse sequence; when k=2, one 90° pulse is followed by $P_2$ 180° pulses; . . . ; and when it is k, one 90° pulse is followed by $P_k$ 180° pulses. Table 1 shows the pulse parameters of a set of CGMF-CPMG of hexadecane and water, where k=4. There are 4 different values of tau and four values of Ne, respectively, the magnetic field gradient is a constant value, which is about 20 gauss/cm, and RD is 12 s. As the adopted waiting time RD is long enough, hydrogen nucleus is fully polarized, so there is no longer dependence on $T_1$. Therefore, in such a condition, the information of diffusion coefficient D and relaxation time $T_2$ is acquired. The principle of the technique is that the intensity of an NMR signal is attenuated due to the Brownian motion of molecules, and such attenuation is related to the diffusion coefficient of fluid molecules. A diffusion effect is generated through changing the value of tau in the CGMF-CPMG pulse sequence in the constant gradient field. The effect of the 90° pulse is to rotate the macro magnetization vector onto the horizontal plane; the effect of continuous 180° pulses is to focus again the signals that are not subject to the phase defocusing caused by diffusion attenuation, and acquire information of other mechanisms of spin echo attenuation $T_2$.

TABLE 1

Pulse Parameters of a Group of CGMF-CPMG of Hexadecane and Water

| k | tau (us) | Ne | G (gauss/cm) | RD (s) |
|---|---|---|---|---|
| 1 | 150 | 30720 | 20 | 12 |
| 2 | 900 | 1536 | 20 | 12 |
| 3 | 1800 | 512 | 20 | 12 |
| 4 | 3000 | 256 | 20 | 12 |

Step B: Acquisition of Two-Dimensional NMR Spectrums

The applications of the NMR technique in the petroleum industry are mainly to measure the signal of saturated fluid hydrogen nucleus in the rock pore by adopting an NMR instrument. These applications are not only related to the fluid itself, but also further influenced by the pore structure of rock. The influence factors of relaxation time of hydrogen nucleus in the fluid include body relaxation, surface relaxation and diffusion relaxation. The body relaxation $T_{2B}$ is the process of energy transfer between the spin nucleus and lattice. The relaxation time is influenced by the spin-spin coupling effect and resonance frequency. The surface relaxation $T_{2S}$ is the mutual effect between pore fluid molecules in a porous medium, and the relaxation time and the surface relaxation rate is related to the specific surface of pore. The diffusion relaxation is related to the diffusion coefficient D, magnetic field gradient G, and pulse interval tau of molecule. Therefore, the expression of the $T_2$ relaxation time in the rock pore is:

$$\frac{1}{T_{2App}} = \frac{1}{T_{2B}} + \frac{1}{T_{2S}} + \frac{1}{T_{2D}} \quad (1)$$

In the equation: $T_{2app}$ is the apparent relaxation time, $T_{2B}$ is the body relaxation time, $T_{2S}$ is the surface relaxation time, and $T_{2D}$ is the diffusion relaxation time.

For $T_{2S}$:

$$\frac{1}{T_{2S}} = \rho \frac{S}{V} \quad (2)$$

where:

$\frac{S}{V}$ is the specific surface of a pore, and $\rho$ is the surface relaxation rate.

For $T_{2D}$:

$$\frac{1}{T_{2D}} = \frac{1}{3} D(\gamma G tau)^2 \quad (3)$$

where: D is the diffusion coefficient of the fluid, $\gamma$ is the gyromagnetic ratio constant, G is the magnetic field gradient, and tau is the pulse time interval.

The signal b(t,tau) measured according to the pulse sequence of the constant gradient field in Step A is generally expressed as:

$$b(t,tau) = \iint f(D,T_2) k_2(t,T_E,D,T_2) dD dT_2 + \epsilon \quad (4)$$

The discrete form is:

$$b_{ik} = \sum_{j=1}^{m} \sum_{l=1}^{p} f_{lj} \exp\left(-\frac{1}{12} \gamma^2 G^2 tau_k^2 D_l t_i\right) \exp(t_i / T_{2j}) + \varepsilon_{ik} \quad (5)$$

Figure 6:
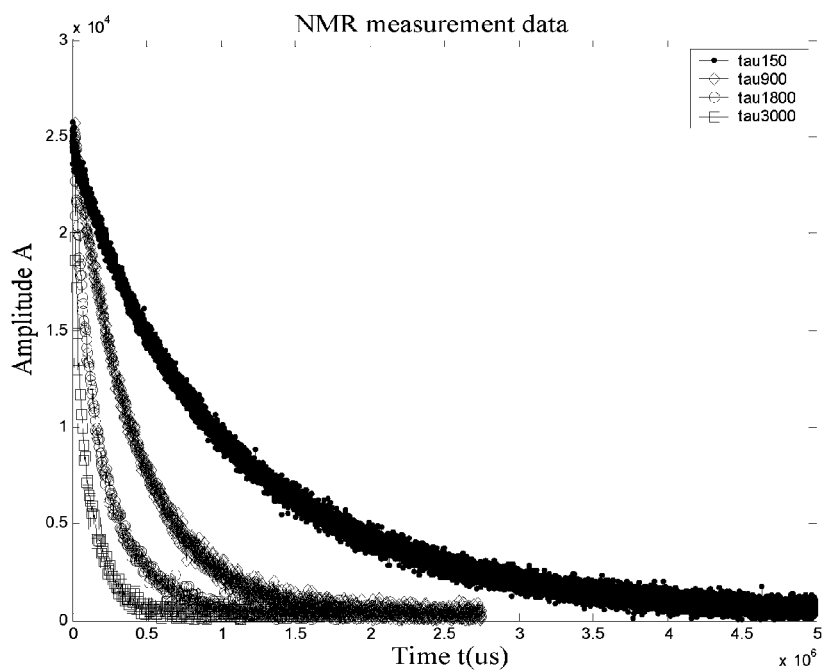
FIG. 6 is a set of multi-exponential attenuation curves of hexadecane and distilled water measured by adopting a CGMF-CPMG pulse sequence.

FIG. 6 shows a set of multi-exponential attenuation curves obtained by measuring hexadecane and water by adopting the pulse sequence parameter in Table 1, and the curve conforms to the rule in Equation 5.

The relaxation time and the diffusion coefficient are uniformly distributed on the axes of a logarithmic coordinate system, and Equation (5) is simplified into:

$$b_{ik} = f_{lj} E_{ik,lj} + \epsilon_{ik} \quad (6)$$

where: $i=1, \ldots, n_k$, $k=1, \ldots, q$, $l=1, p$, and $j=1, \ldots, m$;

i denotes the ith echo of the kth echo train, dimensionless;

k denotes the kth echo train, dimensionless;

l denotes the lth diffusion coefficient selected in advance, dimensionless;

j denotes the jth relaxation time selected in advance, dimensionless;

$n_k$ is the number of echoes of the kth echo train, dimensionless;

q is the number of echo trains of different $tau_k$, dimensionless;

p denotes the number of diffusion coefficients selected in advance;

m denotes the number of relaxation times selected in advance;

$b_{ik}$ denotes the amplitude of the ith echo of the kth echo train with the pulse interval being $tau_k$, dimensionless;

$f_{lj}$ denotes the amplitude when the diffusion coefficient is $D_l$ and the relaxation time is $T_{2j}$, dimensionless;

$$E_{ik,lj} = \exp\left(-\frac{1}{12} \gamma^2 g^2 T_{E_k}^2 D_l t_i\right) \exp(-t_i / T_{2j});$$

$\gamma$ is the gyromagnetic ratio, unit: MHz/T;

G is the magnetic field gradient, unit: Gauss/cm;

$tau_k$ is the pulse interval of the kth echo train, unit: us.

The matrix form of Equation (6) is:

$$\begin{bmatrix} b_{11} \\ \vdots \\ b_{n_1 1} \\ b_{12} \\ \vdots \\ b_{n_2 2} \\ \vdots \\ \vdots \end{bmatrix} = \quad (7)$$

$$\begin{bmatrix} E_{11,11} & \cdots & E_{11,1m} & E_{11,2m} & \cdots & E_{11,pl} & \cdots & E_{11,pm} \\ \vdots & & & & & & & \\ E_{n_1 1,11} & \cdots & & & & & & \\ E_{12,11} & \cdots & & & & & & \\ \vdots & & & & & & & \\ E_{n_2,11} & \cdots & & & & & & \\ \vdots & & & & & & & \\ \vdots & & & & & & & \\ \vdots & & & & & & & \end{bmatrix} \begin{bmatrix} f_{11} \\ \vdots \\ f_{1m} \\ f_{21} \\ \vdots \\ f_{2m} \\ \vdots \\ f_{pl} \\ \vdots \\ f_{pm} \end{bmatrix}$$

Components that are smaller than zero probably exist in the calculated magnitude of the two-dimensional NMR spectrum, which is physically illogical. When Equation 7 is being solved, non-negative constraint further needs to be added, that is, $f_{ij} \geq 0$. The matrix E in Equation 7 is highly singular, the condition number is large, and the practically measured signal cause significant challenges to inversion with noise interferences.

In the present invention, an improved singular value decomposition method is adopted for inversion to acquire a two-dimensional NMR spectrum. The singular value decomposition (SVD) method gives one optimal solution in the sense that $\|Ef-b\|_2$ is minimal, which does not necessarily meet a non-negative constraint condition. In a conventional SVD algorithm, through E reduction iterative solution, the number of dimensions of the solutions is reduced, and the coordinate component that has the largest oscillation is missing. Due to the absence of this part of coordinate component, the spectrum is discontinuous. To acquire a continuous spectrum, the improved singular value decomposition method solves the least squares solutions of $\Delta f$. Assuming that one initial solution $f_0$ is known, make $b_0=Ef_0$, so the original equation may become: $E(f-f_0)=b-b_0$, that is, $E\Delta f=\Delta b$. If the optimal solution $\Delta f$ in the sense of minimal $\|E\Delta f-\Delta b\|_2$ is obtained, $f_0+\Delta f$ is the optimal solution f in the sense of minimal $\|Ef-b\|_2$. As $\Delta f$ is to be solved, during the implementation of non-negative constraints, the matrix E is no longer reduced, and only the components of f that are smaller than zero are changed to zero, and then iterative computation is performed for $\Delta f$ again, until all coordinate components of f meet the non-negative constraints. As E does not change during the iterative solution, singular value decomposition is no longer required for solving the optimal solution in the sense of minimal $\|E\Delta f-\Delta b\|_2$. Compared with the original algorithm, the new algorithm replaces the singular value decomposition process of matrix E with the computation of $\Delta f$ and, and does not need to perform singular value decomposition on the matrix E for cycling each time, which greatly reduces the computation amount and computation time.

Figure 5:
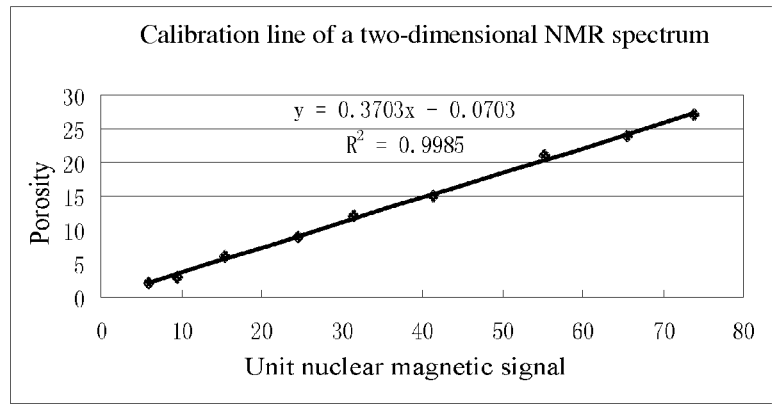
FIG. 5 is a diagram showing the relationship among the two-dimensional NMR spectrum calibration line, the unit volume NMR signal and porosity.
Figure 7:
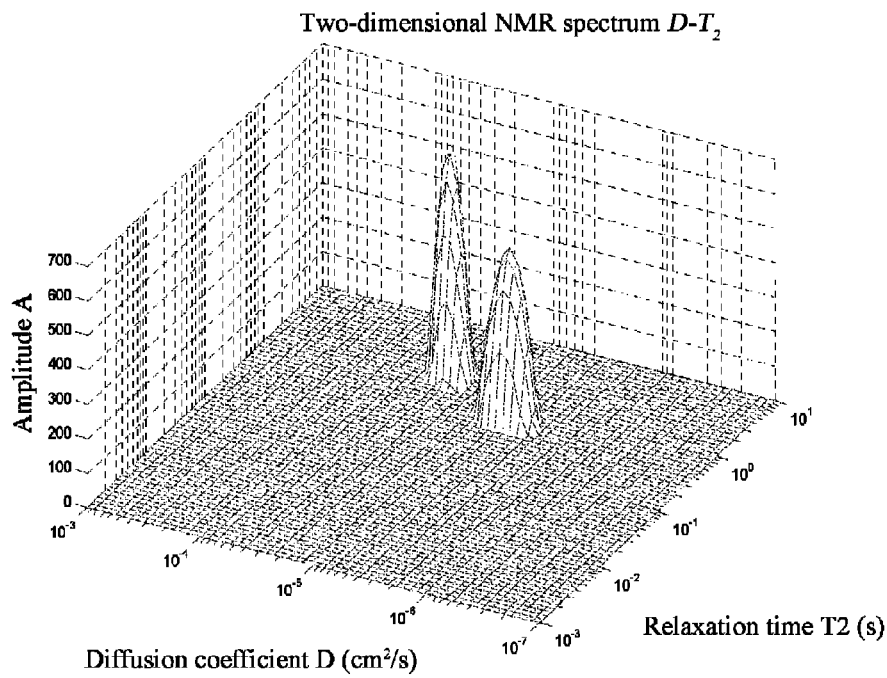
FIG. 7 is a two-dimensional NMR spectrum three-dimensional diagram of hexadecane and water obtained by adopting NMR two-dimensional inversion.
Figure 8:
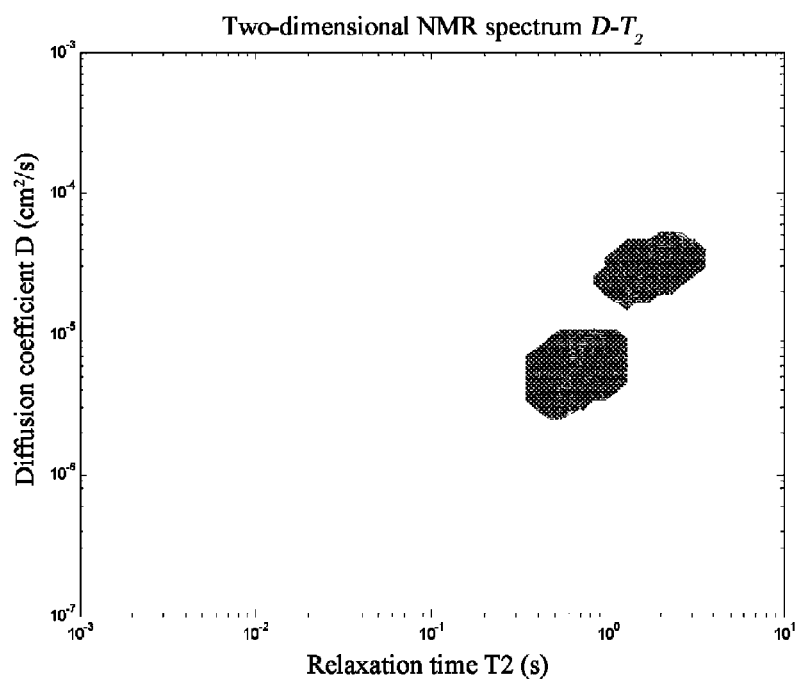
FIG. 8 is a contour line diagram of a two-dimensional NMR spectrum of hexadecane and water obtained by adopting NMR two-dimensional inversion.

FIG. 7 is a two-dimensional NMR spectrum D-$T_2$ three-dimensional diagram of hexadecane and water obtained by adopting NMR two-dimensional inversion on the measurement data of FIG. 6. FIG. 8 is a contour line diagram of a two-dimensional NMR spectrum corresponding to FIG. 7. In the condition of room temperature, the diffusion coefficient of water is about $2.5*10^{-5}$ cm$^2$/s. Therefore, from the two-dimensional NMR spectra in FIG. 7 and FIG. 8, it can be determined that the upper spectrum peak is the signal of water, and the lower spectrum peak is the signal of hexadecane. The diffusion coefficient of water Step C: Calibration of the Constant Gradient Field NMR Calibration is an essential step to measure the sample porosity of a rock in the NMR technique. The calibration of a constant gradient field NMR rock sample analyzer performs measurement and inversion on a standard sample of a constant gradient field by adopting a constant gradient field NMR rock sample analyzer according to Step A and Step B to obtain a two-dimensional NMR spectrum D-$T_2$ of the standard sample and acquire a relationship line between signal and porosity for a unit volume. The constant gradient field NMR standard sample includes 12 in total, and the porosities are 0.5%, 1%, 2%, 3%, 6%, 9%, 12%, 15%, 18%, 21%, 24%, and 27%, respectively. At least 5 are selected for measurement in calibration each time. FIG. 5 shows the two-dimensional NMR spectrum calibration line acquired through calibrating by selecting 9 from the 12. The main steps are as follows:

(1) placing a standard sample with the porosity being 27% in the probe of the constant gradient field NMR rock sample analyzer to perform measurement by adopting a pulse sequence parameter designed in advance to obtain a set of multi-exponential attenuation data;

(2) inputting the porosity of a standard sample with the porosity being 27%, and performing, by constant gradient field two-dimensional NMR spectrum inversion software, inversion and normalization processing on the measurement data of a sample to obtain the signal quantity of a unit volume of the sample;

(3) repeating Step (1) and Step (2) to measure standard samples of different porosities of 24%, 21%, 15%, 12%, 9%, 6%, 3%, and 2%;

(4) performing, by the software system, linear fitting on the measured 9 standard samples automatically to acquire a two-dimensional NMR spectrum calibration curve, and the linearity is 0.9985.

$$y=0.3703x-0.0703$$

Step D: Identification of Fluid Types

According to Step A and Step B, a two-dimensional NMR spectrum D-$T_2$ of a practical rock sample is acquired to identify fluid types. One dimension of the two-dimensional NMR spectrum is a diffusion coefficient D, and the other dimension is relaxation time $T_2$, so that the diffusion coefficient and relaxation time of a sample under test can be acquired at the same time through a two-dimensional NMR spectrum. As bulk phase fluids, for example, crude oil, natural gas and water, not only have different diffusion coefficients, but also have different relaxation time, so that the fluid types may be identified rapidly by adopting a two-dimensional NMR spectrum. The diffusion coefficient of water is related to the temperature. In the condition of room temperature, the diffusion coefficient of water is about $2.5*10^{-5}$ cm$^2$/s. As crude oil has complicated components, the diffusion coefficient is widely distributed, and is about $10^{-7} \sim 10^{-5}$ cm$^2$/s. The crude oil has body relaxation and diffusion relaxation, and the body relaxation time $T_{2B}$ is inversely proportional to the viscosity of crude oil, that is, $T_{2B} \propto \eta^{-1}$; the diffusion coefficient is also inversely proportional to the viscosity of crude oil, that is, $D \propto T/300\eta$ Therefore, a linear relationship exists between the crude oil body relaxation time $T_{2B}$ and the diffusion coefficient D, that is, $D_o \alpha T_2$, where $\alpha \approx 1.045/10^{-5}$ cm$^3$/s$^2$. The diffusion of gas is much faster than that of oil or water and is related to the temperature, pressure and gas density, the distribution range of which is about $10^{-4} \sim 10^{-3}$ cm$^2$/s. As shown in FIG. 7 and FIG. 8, on the two-dimensional NMR spectrum, the water peak and the oil peak are independent from each other, and oil and water may be clearly distinguished according to the attributes of diffusion coefficients of oil and water.

Figure 9A:
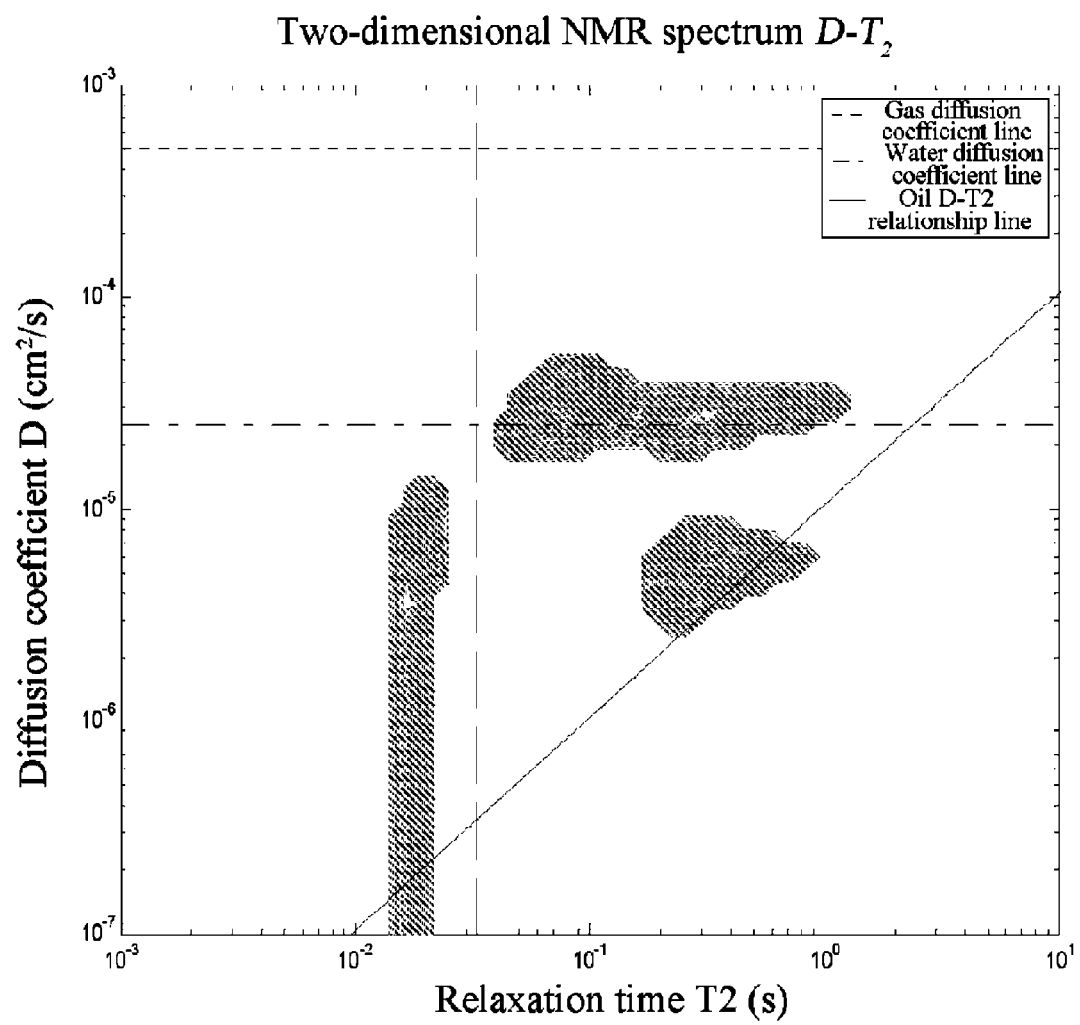
FIG. 9a is a two-dimensional NMR spectrum D-$T_2$ of saturated oil and water in a rock core.
Figure 9B:
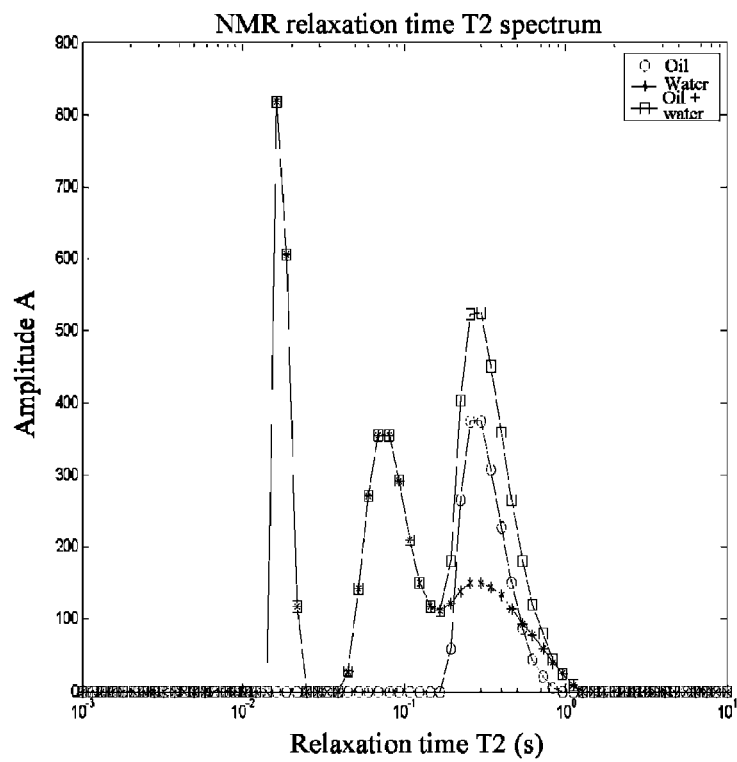
FIG. 9b is a two-dimensional NMR spectrum projection drawing—relaxation time $T_2$ spectrum.
Figure 9C:
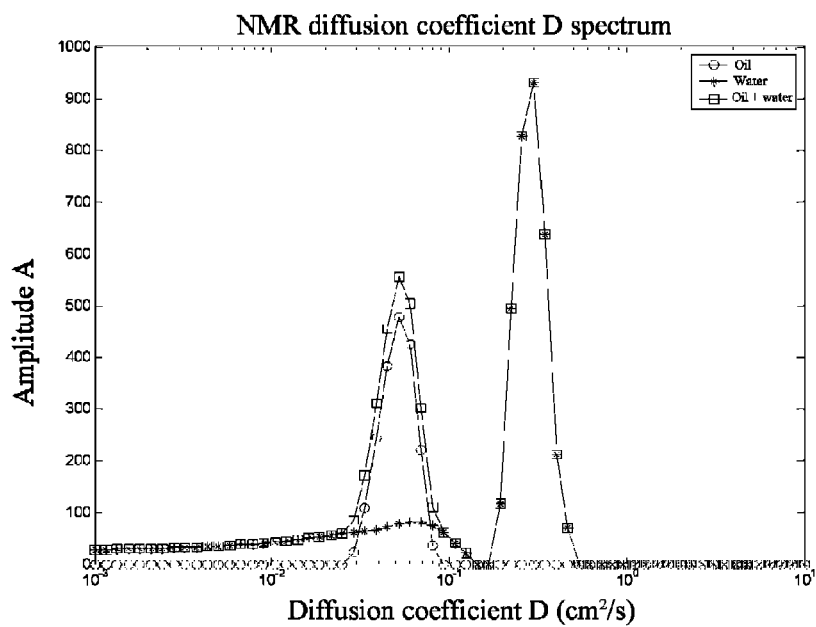
FIG. 9c is a two-dimensional NMR spectrum projection drawing-diffusion coefficient D spectrum.

The constant gradient field NMR rock sample analyzer software has established the template of two-dimensional NMR spectrum to identify fluid types according to the properties of diffusion coefficient and relaxation time of oil, gas and water. FIG. 9a is the two-dimensional NMR spectrum D-$T_2$ of saturated oil and water in a rock core, FIG. 9b is the two-dimensional NMR spectrum projection drawing-relaxation time $T_2$ spectrum of FIG. 9a, FIG. 9c is the two-dimensional NMR spectrum projection drawing-diffusion coefficient D spectrum of FIG. 9a. For the two horizontal lines in FIG. 9a, the one above is the diffusion coefficient line of gas, and the one below is the diffusion coefficient line of water, and the oblique line on the right is the D-$T_2$ relationship line of oil. In FIG. 9a, the spectrum peak in the D-$T_2$ relationship line is the signal of oil, and the other is the signal of water. As the rock sample is fully saturated with oil and water, and the rock sample is highly hydrophilic, the oil phase is dominated by body relaxation and diffusion relaxation, and the rest is surface relaxation. Therefore, the oil phase is slightly subject to the pore surface effect, and the relaxation time and the diffusion coefficient are closes to those of the bulk phase status. As the rock sample is highly hydrophilic, water is affected by body relaxation, diffusion relaxation and surface relaxation together. Therefore, water phase is significantly subject to the pore surface force, and the relaxation time and diffusion coefficient are influenced to different degrees, resulting in that on one-dimensional relaxation time $T_2$ spectrum and one-dimensional diffusion coefficient D spectrum, a part of signals of oil and water overlap each other, making direct distinguishing impossible, as shown in FIG. 9b and FIG. 9c. The two-dimensional NMR spectrum D-$T_2$ adds one-dimensional diffusion coefficient on the basis of the one-dimensional relaxation time $T_2$ spectrum, so that the fluid types in the pore can be better identified from the 3D space.

Step E: Computation of Petrophysical Parameters

The petrophysical parameters are computed according to the two-dimensional NMR spectrum D-$T_2$ of a practical rock sample acquired in Step D. The constant gradient field NMR rock sample analyzer is applicable to the measurement of relaxation and diffusion properties of a fluid, and particularly fluid properties in a rock pore. As these properties are different for oil, gas and water, the constant gradient field NMR rock sample analyzer can provide the proportion of oil, gas and water, and parameters such as rock porosity, permeability, oil saturation, movable fluid saturation, crude oil coefficient. By taking the rock sample shown in FIG. 9a as an example, the above parameters are computed respectively, for the rock sample, the conventional porosity is 14.28%, the permeability is 50.8 mD, and the oil saturation is 33.98%.

(1) Porosity

The NMR technique directly detects the hydrogen nucleuses ($^1$H) in a sample under test and may accurately measure the amount of fluid in the pores of a rock sample. When the pores of the rock sample are filled with a fluid, the fluid amount is equal to the pore volume. Therefore, the porosity of the rock sample may be accurately measured by using the NMR technique. When the two-dimensional NMR spectroscopy is adopted to measure the porosity of a rock sample, first, it has to be guaranteed that the rock sample is fully saturated; next, calibration is performed by adopting a constant gradient field NMR standard sample to acquire a calibration line of the two-dimensional NMR spectrum, that is, the relationship line between the NMR signal for a unit volume and the porosity; finally, the measured NMR signal of the fluid in the saturated rock sample is calibrated using the calibration line to acquire the NMR porosity of the rock sample. It is obtained according to Equation 17 that for the measured rock sample in FIG. 9a, the porosity x=2.7*(y+0.0703)=2.7*(5.2186+0.0703)=14.28.

(2) Movable Fluid Saturation

The relaxation time spectrum $T_2$ reflects the distribution of pore diameters of a rock. When the pore diameter is small to a certain degree, the fluid in the pore is constrained by the capillary force and fails to flow. Therefore, a limit exists on the $T_2$ relaxation time spectrum. When the relaxation time of pore fluid is greater than a certain relaxation time, the fluid is a movable fluid, and otherwise it is an irreducible fluid. Such a relaxation time limit is referred to as the cutoff value of the movable fluid. The cutoff value of the movable fluid $T_2$ usually needs to be determined by combining the NMR and centrifugation. The cutoff value on the one-dimensional relaxation time $T_2$ spectrum is a cutoff line on the two-dimensional NMR spectrum. The vertical line in FIG. 9a is the cutoff line of the movable fluid of the two-dimensional NMR spectrum of the rock sample. According to the two-dimensional NMR spectrum explanation template, that is, the cutoff line of movable fluid, diffusion coefficient line, oil phase relationship line, it may be comprehensively judged and selected that the portion on the right of the cutoff line of the movable fluid is the movable fluid area, the system automatically computes a ratio between the volume integral of the selected area and the total volume integral, and the movable fluid saturation is 80.86%. The irreducible fluid saturation is 100%−80.86%=19.14%. The movable fluid saturation has become one important index for reservoir evaluation, and the research on movable fluid saturation is very important for exploration and development of low permeability oil fields.

(3) Oil Saturation

Oil saturation is one of the key parameters for evaluating the quality of an oil field reservoir. The key for the measurement of oil saturation is to distinguish oil and water. The two-dimensional NMR spectroscopy may measure the relaxation time and diffusion coefficient of oil and water, and fluid types can be rapidly identified according to the two-dimensional NMR spectrum explanation template to distinguish oil and water. The constant gradient field NMR rock sample analyzer software adopts a click and selection manner to compute oil saturation. For example, in FIG. 9a, the spectrum peak on the D-$T_2$ relationship line in the two-dimensional NMR spectrum may be selected as the area of oil with a mouse, and the computer automatically computes a ratio between the volume integral of the selected area and the total volume integral. The oil saturation is 31.19%. As the rock sample is only saturated with oil and water, the water saturation is 68.81%.

(4) Permeability

The two-dimensional NMR spectrum reflects the formation pore diameter distribution, whereas a certain relationship exists between the formation rock permeability and the pore diameter (pore throat). Therefore, the permeability of the rock sample may be computed according to the two-dimensional NMR spectrum. The test shows that the empirical Equation 11 may be adopted to compute the permeability of a rock sample.

$$K_{nmr} = \left(\frac{\phi_{nmr}}{C}\right)^4 \left(\frac{100\% - S_{wi}}{S_{wi}}\right)^2 = \left(\frac{13.47}{9}\right)^4 \left(\frac{100\% - 19.14\%}{19.14\%}\right)^2 = 89.55 \quad (11)$$

where, $K_{nmr}$ is the NMR permeability, $\phi_{nmr}$ is the NMR porosity, $S_{wi}$ the irreducible water saturation, C is a coefficient to be determined, which has regional empiricism and needs to be precisely determined through indoor NMR rock core analysis, and in China is mainly between 3 and 12. The NMR permeability computed according to the empirical Equation 11 desirably solves the problem of small NMR permeability of rock sample having high oil saturation and high oil density during the computation according to Coates model.

(5) Crude Oil Coefficient

Crude oil with different properties has a different NMR signal quantity in unit volume. This is because crude oil has complicated components and the contents of all components are different. As high-density crude oil has a large quantity of heavy components, especially heavy oil has high colloidal asphaltene, the ratio of carbon and hydrogen is large, and the unit volume NMR has a small signal quantity. Therefore, when a rock sample contains crude oil with a high viscosity, the NMR signal for a unit volume of measured rock sample is small, causing offsets of different degrees to the parameters of a rock sample, such as permeability, movable fluid saturation and oil saturation, which have to be calibrated. For example, for a standard sample with the porosity equal to 24%, and the NMR signal quantity of a unit volume is 1258. The NMR signal quantity of a unit volume of certain crude oil is 4680, according to Equation 12, it may be obtained that the crude oil coefficient $$\eta = \frac{1258/0.24}{4680} = 1.12,$$

dimensionless. After the crude oil coefficient is input, the constant gradient field NMR rock sample analyzer automatically modifies parameters of the rock sample such as porosity, permeability, oil saturation, movable fluid saturation according to Equations 15 to 17.

Step F: Acquisition of Axial Saturation Distribution of a Rock Sample

The slicing thickness of the constant gradient field NMR rock sample analyzer is 0.3 cm, and according to Step A to Step F, slice scanning may be performed on a rock sample to acquire partial oil and water saturation of a rock sample; at the same time, Step A to Step F are repeated to perform continuous slice scanning on the rock sample to acquire axial oil and water saturation distribution and movable fluid saturation distribution of the rock sample, so as to perform better real-time reservoir evaluation and fluid identification, especially the evaluation of oil and gas reservoirs of low porosity, low permeability and complicated reservoir.

INDUSTRIAL APPLICABILITY

Figure 10:
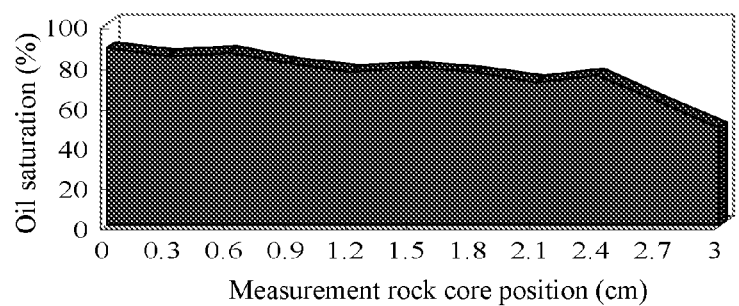
FIG. 10 shows axial oil saturation distribution inside a rock core acquired by multiple times of slice scanning on a rock sample.
Figure 11:
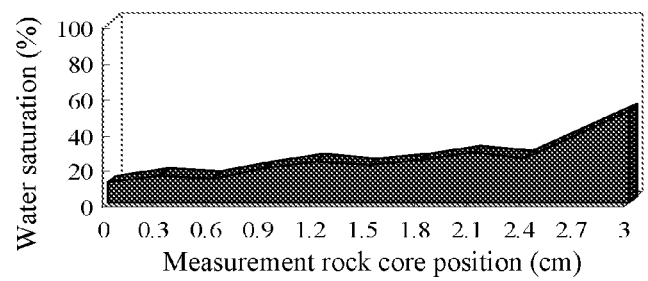
FIG. 11 shows axial water saturation distribution inside a rock core after multiple times of slice scanning on a rock sample.

The present invention provides constant gradient field NMR rock sample analysis. For the rock selected for the test, the core porosity is 23.82% and the permeability is 12.44 mD. By adopting a displacement test, the rock core reaches a irreducible water saturated oil status, and the final water discharge is 2.89 ml. It is computed that the oil saturation is 77.62%. As shown in FIG. 10 and FIG. 11, the axial oil and water saturation distributions of a rock core measured by adopting the two-dimensional NMR spectrum in a saturated oil irreducible water status are shown, respectively. At the inlet end, the oil saturation is up to 88.42% and is higher than the conventional oil saturation by 10.8%. The oil saturation gradually decreases from the inlet end to an outlet end. From the inlet end to the 2.4 cm position, the oil saturation decreases gradually. From the 2.4 cm position to the outlet end, the decrease amplitude of oil saturation greatly increases. Particularly, at the 3.0 cm position of the outlet end, the oil saturation decreases to 48.63% and becomes lower than the conventional oil saturation 28.99%. Due to the end effect of the outlet end, the oil saturation is relatively low and a irreducible water status fails to be reached. Generally speaking, the two-dimensional NMR spectrum may measure the axial oil saturation distribution inside a rock core, the average value of oil saturation of the whole rock core is 75.41%, and the absolute error is 2.21% with the conventional oil saturation. The axial water saturation of the rock core is opposite to the oil saturation phase, as shown in FIG. 11. From the inlet end to the outlet end, the oil saturation of the rock core after displacement generally decreases and the water saturation increases; however, partially the oil and water saturation are uneven, which is mainly caused by the capillary force effect, Jamin effect, fingering effect, and the like in the displacement process, resulting in that the oil and water distribution in the rock core is not uniform.

The present invention provides a constant gradient field NMR rock sample analyzer. The instrument adopts a gradient field design and two-dimensional inversion, so that not only a one-dimensional relaxation time $T_2$ spectrum may be acquired and petrophysical parameters such as pore structure, porosity, permeability, oil saturation, movable fluid saturation may be provided, but also the constant gradient field NMR rock sample analyzer may perform slice scanning and provide diffusion coefficients of oil, gas and water, viscosity of crude oil, porosity distribution, oil and water saturation distribution, so as to perform better real-time reservoir evaluation and fluid identification, and particularly the evaluation of oil and gas reservoir having low porosity and low permeability and complicated reservoir.

The constant gradient field NMR rock sample analyzer may be placed with a high-temperature high-pressure probe to simulate the borehole operation of an NMR logging tool, which provides new technical means for researches on the seepage mechanism of fluids in a formation status inside a laboratory, and provide new methods for understanding and solving technical bottlenecks during the research and development of an NMR logging tool.

What is claimed is:

1. A constant gradient field nuclear magnetic resonance (NMR) rock sample analysis method, characterized in that it comprises:

1) in a constant gradient field generated by a magnet, according to a saturated fluid in a sample under test, designing parameters comprising an echo train k, a pulse interval tau, the number of 180° pulses Ne, and a waiting time RD in a CGMF-CPMG pulse sequence to perform NMR measurement to acquire measurement data; the value of k is between 2 and 8, the value of tau is distributed between 150 μs and 20000 μs, the value of Ne is distributed between 128 and 30720, and the waiting time is distributed between 2000 ms and 12000 ms;

2) converting NMR data measured in Step 1) into a two-dimensional NMR spectrum $D$-$T_2$; the data measured by adopting the CGMF-CPMG pulse sequence conforms to a multiexponential attenuation rule:

$$b_{ik} = \sum_{j=1}^{m}\sum_{l=1}^{p} f_{lj}\exp\left(-\frac{1}{12}\gamma^2 g^2 tau_k^2 D_l t_i\right)\exp(t_i/T_{2j}) + \varepsilon_{ik} \qquad (5)$$

wherein: i=1, ..., $n_k$, k=1, ..., q, l=1, p, and j=1, ..., m;
i denotes the ith echo of the kth echo train, dimensionless;
k denotes the kth echo train, dimensionless;
l denotes the lth diffusion coefficient selected in advance, dimensionless;
j denotes the jth relaxation time selected in advance, dimensionless;
$n_k$ is the number of echoes of the kth echo train, dimensionless;
q is the number of echo trains of different $tau_k$, dimensionless;
p denotes the number of diffusion coefficients selected in advance;
m denotes the number of relaxation times selected in advance;
$b_{ik}$ denotes the amplitude of the ith echo of the kth echo train with the pulse interval being $tau_k$, dimensionless;
$f_{lj}$ denotes the amplitude when the diffusion coefficient is $D_l$, and the relaxation time is $T_{2,j}$, dimensionless;
γ is the gyromagnetic ratio, unit: MHz/T;
G is the magnetic field gradient, unit: Gauss/cm;
$tau_k$, is the pulse interval of the kth echo train, unit: us;
and performing inversion on Equation (5) by adopting an improved singular value de composition method to acquire the two-dimensional NMR spectrum $D$-$T_2$;

3) performing measurement and inversion on a constant gradient field standard sample using Step 1) and Step 2) to obtain the two-dimensional NMR spectrum $D$-$T_2$ of the standard sample; taking 12 constant gradient field NMR standard samples, porosities being 0.5%, 1%, 2%, 3%, 6%, 9%, 12%, 15%, 18%, 21%, 24%, and 27%, respectively, for each time of calibration, select at least 5 of the 12 for measurement and inversion to obtain two-dimensional NMR spectra of standard samples with different porosities, then performing volume integration on the two-dimensional NMR spectra to obtain NMR signals of the standard samples; the ratio between the NMR signal and the volume of the standard sample being the NMR signal of a unit volume; and performing linear fitting on porosity and the NMR signal of the unit volume to obtain a relationship line thereof:

$$y = ax + b \qquad (8)$$

wherein y represents the NMR signal quantity of a unit volume, x represents an NMR porosity (%), a represents a slope, and b represents a Y-intercept;
when measuring the rock sample, measuring the NMR signal of a unit volume of the rock sample to compute the porosity of a rock sample;

4) measuring the rock sample using Step 1) and Step 2), acquiring a fluid two-dimensional NMR spectrum $D$-$T_2$ in the rock sample, performing fluid types identification according to a practically measured two-dimensional NMR spectrum $D$-$T_2$ of the rock sample; wherein the diffusion coefficient of water is a constant, and is related to the temperature; the diffusion coefficient of gas is related to the temperature and pressure; and a linear relationship exists between the diffusion coefficient and relaxation time of crude oil;

$$D_w(T_2) = D_w(T) \qquad (9)$$

$$D_g(T_2) = D_g(T, P) \qquad (10)$$

$$D_o = \alpha T_2 \qquad (11)$$

establishing, by a constant gradient field NMR rock sample analyzer, according to these NMR attributes of diffusion coefficient and relaxation time of oil, gas and water, a two-dimensional NMR spectrum explanation template, and dividing oil, gas and water according to the positions of the practically measured two-dimensional NMR spectrum $D$-$T_2$ of the rock sample in the explanation template to rapidly identify fluid types;

5) computing the porosity, permeability, oil saturation, movable fluid saturation, crude oil coefficient of the rock sample according to the two-dimensional NMR spectrum $D$-$T_2$ of fluids in the rock sample acquired in Step 4);

a) performing volume integration through the two-dimensional NMR spectrum of the rock sample, introducing a constant gradient field NMR calibration line according to Step 3), and computing the NMR porosity of the rock sample;

b) computing the permeability of the rock sample according to the NMR porosity and irreducible water saturation:

$$K_{nmr} = \left(\frac{\phi_{nmr}}{C}\right)^4 \left(\frac{100\% - S_{wi}}{S_{wi}}\right)^2 \qquad (12)$$

wherein, $K_{nmr}$ is NMR permeability, $\Phi_{nmr}$ is NMR porosity, $S_{wi}$ is irreducible water saturation, and C is the coefficient to be determined;

c) identifying fluid types rapidly according to the two-dimensional NMR spectrum explanation template established in Step 4), distinguishing oil and water; selecting the area of oil in the two-dimensional NMR spectrum with a mouse, computing, by the system, automatically the ratio between the volume integral of the selected area and the total volume integral of the two-dimensional NMR spectrum, and acquiring oil saturation; similarly, obtaining oil, gas and water saturation, respectively;

d) comprehensively judging and selecting a movable fluid area according to a movable fluid $T_2$ cutoff line, a diffusion coefficient line, an oil phase relationship line in the two-dimensional NMR spectrum explanation template established in Step 4), computing, by the system, automatically the ratio between the volume integral of the selected area and the total volume integral to acquire movable fluid saturation;

e) when the rock sample contains crude oil with a high viscosity, measuring that the NMR signal of a unit volume of rock sample is small, causing offsets of different degrees to parameters of the porosity, permeability, movable fluid saturation and oil saturation of a rock sample, wherein calibration is required; the crude oil coefficient is ratio between the signal of a unit volume of constant gradient field NMR standard sample and the NMR signal of a unit volume of crude oil:

$$\eta = \frac{A_{Standard\ Sample}/\phi_{Standard\ Sample}}{A_{Crude\ Oil}} \quad (13)$$

wherein: $\eta$ is the crude oil coefficient, $A_{Standard\ Sample}$ is the NMR signal quantity of a unit volume of the standard sample, $\Phi_{Standard\ Sample}$ is the porosity of and standard sample, and $A_{Crude\ Oil}$ is the NMR signal quantity of a unit volume of the measured crude oil;

6) the slicing thickness of the constant gradient field NMR rock sample analyzer being 0.3 cm, and according to Step 1) to Step 5), performing single slice scanning on a rock sample to acquire partial oil and water saturation of a rock sample; at the same time, repeating Step 1) to Step 5) to perform continuous slice scanning on the rock sample to acquire axial oil and water saturation distribution and movable fluid saturation distribution of the rock sample, so as to perform better realtime reservoir evaluation and fluid identification.

2. The method according to claim 1, characterized in that: after the crude oil coefficient is introduced, as both the signal and total signal of the crude oil have changed, the movable fluid saturation, irreducible water saturation, movable water saturation need to be computed by selecting an area again according to the explanation template; the equations need to be modified for porosity, permeability, and oil saturation:

the modified equation of oil saturation by the crude oil coefficient:

$$S_{Oil,Modified} = \frac{A_{Oil} \times \eta}{A_{Water} + A_{Oil} \times \eta} \times 100\% \quad (15)$$

the modified equation of porosity by the crude oil coefficient:

$$\phi_{Modified} = \frac{1}{a}(A_{Oil} \times \eta + A_{Water} - b)/100\% \quad (16)$$

the modified equation of permeability by the crude oil coefficient:

$$K_{Modified} = \left(\frac{\phi_{Modified}}{C}\right)^4\left(\frac{1-S_{wi,Modified}}{S_{wi,Modified}}\right)^2 \quad (17)$$

wherein, $\phi_{Modified}$ is the modified NMR porosity, $K_{Modified}$ is the modified NMR permeability, $\eta$ is the crude oil coefficient, $S_{Oil,\ Modified}$ is the modified oil saturation, $A_{Oil}$ is the oil signal quantity, $A_{Water}$ is the water signal quantity, and $S_{wi,\ Modified}$ is the modified constrained water saturation.

3. The constant gradient field NMR rock sample analyzer according to claim 1, characterized in that: the analyzer is formed of a measuring device and a control system; the measuring device is formed of a gradient magnet, a probe and a temperature control system; the gradient magnet is one enclosed cavity, the probe is located at the central position of the gradient magnet cavity, the probe and the control system are connected to a T/R matching circuit of the control system through an electrical cable; and the control system is connected to a computer through a USB port.

4. The constant gradient field NMR rock sample analyzer according to claim 3, characterized in that: the gradient magnet of the constant gradient field NMR rock sample analyzer is formed of a yoke plate, a magnetic steel, a polar plate, and a side yoke plate; the yoke plate and the side yoke plate form the gradient magnet cavity, the magnetic steel is connected to the yoke plate, the polar plate has a cross section being a trapezoidal structure, and is connected to the magnetic steel; the yoke plate, the polar plate, and the side yoke plate are machined from an electrical pure iron DT4C material, the magnetic steel is made of a 2:17 SmCo magnetic material; the magnetic steel and the yoke plate, and the polar plate and the magnetic steel are adhered by using the glue BJ-39; the gradient magnet generates a magnetic field $B_0$ that is uniform longitudinally and has horizontal gradients to form a sample detection area, the magnetic field direction is along the z-axis, the gradient direction is along the x-axis; the angle between two polar plates is between 10° and 30°, an air gap formed between the two polar plates is between 150 mm and 364 mm; a group of temperature control system is disposed at the outer surface of the gradient magnet, and performs constant temperature control between 10° and 60° on the gradient magnet, so as to reduce the influences of temperature on the measurement result of the instrument.

5. The constant gradient field NMR rock sample analyzer according to claim 3, characterized in that: the probe of the constant gradient field NMR rock sample analyzer is formed of one nonconductive circular sample tube and a loop circuitry; the loop circuitry is wound on the sample tube; the loop circuitry is a solenoid coil, a saddle coil or other applicable coils; the probe is capable of transmitting an excitation signal to a sample to be tested in a radio frequency manner as a transmitter and receiving NMR information as a receiver; and a sample detection area is provided inside the probe.

6. The constant gradient field NMR rock sample analyzer according to claim 3, characterized in that: the control system of the constant gradient field NMR rock sample analyzer is formed of a main controller, a frequency generator, a power amplifier, a T/R matching circuit, a preamplifier, a receiver and an A/D converter with a buffer; the main controller generates and transmits a pulse sequence for exciting an NMR signal, receives an NMR echo signal and performs computation processing on the signal and performs an upload to the computer, the main controller and the computer are interconnected and perform data transmission through a USB interface; the frequency generator and the main controller are interconnected through an electrical cable, the frequency generator performs electrical current driving on the an NMR excitation signal generated by the main controller, the generated signal is sent to the power amplifier for power amplification; the power amplifier and the frequency generator are interconnected through an electrical cable, the power amplifier amplifies the signal to hundreds of Watts for exciting the NMR information of the sample to be tested; the probe and the transmitter/receiver T/R matching circuit comprise a resonance capacitor, a T/R switch and an impedance matching circuit, and the power amplifier is connected to the preamplifier through an electrical cable; the T/R transmission/reception switch accomplishes a transmission/reception conversion process; the impedance matching circuit is used for performing impedance matching on a radio frequency circuit; the preamplifier amplifies the NMR echo signal by 70 DB, the magnitude thereof is amplified and then collected and received by the receiver, and is then output to the main controller by the A/D converter with a buffer, so as to provide output data required for subsequent use and analysis; and the preamplifier and the receiver, and the receiver and the A/D converter are connected through an electrical cable.

* * * * *